United States Patent
Kim et al.

(10) Patent No.: US 12,416,447 B2
(45) Date of Patent: Sep. 16, 2025

(54) CARBON DIOXIDE REUSING SYSTEM AND METHOD

(71) Applicant: SAMSUNG ELECTRONICS CO., LTD., Suwon-si (KR)

(72) Inventors: Jin Soo Kim, Hwaseong-si (KR); Myung Beom Park, Seoul (KR); Dong-Min Kang, Seoul (KR); Sam Jong Choi, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 937 days.

(21) Appl. No.: 17/543,168

(22) Filed: Dec. 6, 2021

(65) Prior Publication Data
US 2023/0008927 A1 Jan. 12, 2023

(30) Foreign Application Priority Data
Jul. 9, 2021 (KR) .................. 10-2021-0090144

(51) Int. Cl.
*F25J 3/02* (2006.01)
*C01B 32/50* (2017.01)
(Continued)

(52) U.S. Cl.
CPC .............. *F25J 3/0266* (2013.01); *C01B 32/50* (2017.08); *G01N 1/2226* (2013.01); *G01N 1/2247* (2013.01); *G01N 33/004* (2013.01)

(58) Field of Classification Search
CPC .............. F25J 3/0266; C01B 32/50; C01B 2210/0062; G01N 1/2226; G01N 1/2247;
(Continued)

(56) References Cited

U.S. PATENT DOCUMENTS

| | | | |
|---|---|---|---|
| 7,080,651 B2 | 7/2006 | Mizobata et al. | |
| 2005/0006310 A1* | 1/2005 | Agrawal | B08B 3/14 |
| | | | 210/741 |
| 2016/0265840 A1 | 9/2016 | Le Bot | |

FOREIGN PATENT DOCUMENTS

| | | | | |
|---|---|---|---|---|
| CN | 1238232 A | * | 12/1999 | ........... B01D 53/002 |
| FR | 3075383 A1 | * | 6/2019 | ........... G01N 1/2202 |

(Continued)

OTHER PUBLICATIONS

Translation of WO 2007088880 A1, Webin (Year: 2007).*
(Continued)

*Primary Examiner* — Anthony J Zimmer
*Assistant Examiner* — Starfari Teshawn Mcclain
(74) *Attorney, Agent, or Firm* — Sughrue Mion, PLLC (57) ABSTRACT

A system and a method for reusing carbon dioxide are provided. The system includes: a process apparatus configured to discharge exhaust gas containing carbon dioxide therefrom; a purifying device configured to purify the exhaust gas, and thus produce reused carbon dioxide from the exhaust gas and store the produced reused carbon dioxide; a first supply tank configured to receive the reused carbon dioxide from the purifying device; a second supply tank configured to receive the reused carbon dioxide from the first supply tank and provide the reused carbon dioxide to the process apparatus; and a blocking device configured to, based on determining that a purity of the reused carbon dioxide provided from the purifying device to the first supply tank fails to satisfy a predefined reference, block flow of the reused carbon dioxide from the purifying device to the first supply tank.

11 Claims, 7 Drawing Sheets

(51) Int. Cl.
*G01N 1/22* (2006.01)
*G01N 33/00* (2006.01)

(58) Field of Classification Search
CPC .......... G01N 33/004; G01N 2030/025; B01D 53/75; B01D 46/0027; B01D 53/002; B01D 53/04; B01D 53/26; B01D 53/30; B01D 53/86; B01D 2257/504; B01D 2258/0216; C01P 2006/80; Y02C 20/40
See application file for complete search history.

(56) References Cited

FOREIGN PATENT DOCUMENTS

| | | | | |
|---|---|---|---|---|
| JP | 2017176954 A | * | 10/2017 | |
| JP | 6353379 B2 | | 7/2018 | |
| KR | 1020040058207 A | | 7/2004 | |
| KR | 101047862 B1 | | 7/2011 | |
| KR | 101284395 B1 | | 7/2013 | |
| KR | 1020130091550 A | | 8/2013 | |
| KR | 102064612 B1 | | 1/2020 | |
| KR | 1020200084068 A | | 7/2020 | |
| WO | WO-2007088880 A1 | * | 8/2007 | ......... B01D 11/0492 |

OTHER PUBLICATIONS

Translation of JP-2017176954-A, Naito (Year: 2017).*
Translation of FR-3075383-A1, Blanc (Year: 2019).*
Tanslation of CN-1238232-A, Novak (Year: 1999).*

* cited by examiner

CARBON DIOXIDE REUSING SYSTEM AND METHOD

CROSS-REFERENCE TO THE RELATED APPLICATION

This application claims priority from Korean Patent Application No. 10-2021-0090144 filed on Jul. 9, 2021 in the Korean Intellectual Property Office, and all the benefits accruing therefrom under 35 U.S.C. 119, the contents of which in its entirety are herein incorporated by reference.

BACKGROUND

Field

Embodiments of the present disclosure relate to a carbon dioxide recycling system. More specifically, embodiments of the present disclosure relate to a carbon dioxide reusing system by which in a process of purifying and storing carbon dioxide in an exhaust gas discharged from a process apparatus, and then supplying the reused purified carbon dioxide to the process apparatus, when a purity of reused carbon dioxide does not satisfy a predefined reference, the reused carbon dioxide is prevented from being supplied to the process apparatus.

Description of Related Art

Carbon dioxide is generally known as a major cause of global warming. However, carbon dioxide occupies a significant share in a gas market, and may be used in a metal industry such as welding, a food and beverage industry related to producing and processing of food or beverages, and a transportation industry such as transportation using dry ice. Considering a proportion of carbon dioxide use in various industries, the use of carbon dioxide is important.

In one example, the government recently announced the "2050 Carbon Neutral Promotion Strategy". Carbon neutrality means that emission of greenhouse gases caused by human activities is reduced as much as possible, and actual carbon dioxide emission becomes zero via absorption by forests or artificial removal of remaining greenhouse gases. This may be due to abnormal climate that has occurred around the world due to global warming.

Based on the government's announcement, the Ministry of Science and Technology announced the "2050 Carbon Neutral Technology Innovation Promotion Strategy". This may determine key fields in which carbon neutrality is achieved, derive core fields with a high contribution to reducing greenhouse gas emissions, and securing 10 carbon-neutral core technologies in consideration of advancement of key industries and basic technologies, thereby minimizing the carbon emissions.

In particular, in a semiconductor industry, need for reuse of carbon dioxide has emerged as an alternative technology to an existing process gas (F-GAS; fluorinated gases) and an optimal management system for greenhouse gases is required. In a semiconductor process, carbon dioxide may be used in various processes such as a supercritical process and an exposure process.

In one example, as semiconductors are rapidly becoming highly integrated, carbon dioxide used in the semiconductor processes requires high purity. Carbon dioxide used in recent semiconductor processes is generally required to have a purity of 9-to-6, that is, 99.9999%. Accordingly, when carbon dioxide that does not meet the required purity is used in the semiconductor process, fatal problems such as generation of defective products and shutdown of all of semiconductor facilities may occur.

In a conventional semiconductor process, purifying has been performed via oxidation or other methods to obtain carbon dioxide of high purity as described above. Further, in a process of reusing used carbon dioxide, various impurities that may occur during the purifying process or impurities still remaining after the purifying process may be contained in the reused carbon dioxide. However, conventionally, a scheme of controlling supply the reused carbon dioxide to the process apparatus when the purity of the reused carbon dioxide is not satisfied is absent, and thus, a poor process is performed and various problems may occur.

SUMMARY

Embodiments of the present disclosure provide a carbon dioxide reusing system by which when a quality of reused carbon dioxide does not meet a preset reference in a process of purifying and re-supplying carbon dioxide used in the process apparatus, the supply thereof to the process apparatus is prevented, thereby avoiding risks caused due to carbon dioxide having an out-of-reference purity in the process.

Benefits of embodiments of the present disclosure are not limited to the above-mentioned benefit. Other purposes and advantages of embodiments of the present disclosure that are not mentioned may be understood based on following descriptions, and may be more clearly understood based on the non-limiting example embodiments according to the present disclosure. Further, it will be easily understood that the purposes and advantages of embodiments of the present disclosure may be realized using means shown in the claims and combinations thereof.

According to embodiments, a system for reusing carbon dioxide is provided. The system includes: a process apparatus configured to discharge exhaust gas containing carbon dioxide therefrom; a purifying device configured to purify the exhaust gas, and thus produce reused carbon dioxide from the exhaust gas and store the produced reused carbon dioxide; a first supply tank configured to receive the reused carbon dioxide from the purifying device; a second supply tank configured to receive the reused carbon dioxide from the first supply tank and provide the reused carbon dioxide to the process apparatus; and a blocking device configured to: determine whether a purity of the reused carbon dioxide provided from the purifying device to the first supply tank satisfies a predefined reference; and based on determining that the purity of the reused carbon dioxide provided from the purifying device to the first supply tank fails to satisfy the predefined reference, block flow of the reused carbon dioxide from the purifying device to the first supply tank.

According to one or more embodiments, while the blocking device blocks the flow of the reused carbon dioxide, the first supply tank is configured to provide previously stored reused carbon dioxide therein to the second supply tank.

According to one or more embodiments, the system further includes: a first pipe that connects the purifying device to the first supply tank; and a valve installed at the first pipe, the valve configured to block the flow of the reused carbon dioxide to the first supply tank, wherein the blocking device includes: a sampler configured to sample the reused carbon dioxide in the first pipe; a first analyzer configured to determine whether the purity of the sampled reused carbon dioxide satisfies the predefined reference, and generate an analyzing result of the purity of the sampled reused carbon dioxide; and a controller configured to receive the analyzing result and provide a control signal based on the analyzing result to the valve.

According to one or more embodiments, the purifying device includes: a collector configured to collect the exhaust gas; a purifier configured to purify the collected exhaust gas to produce the reused carbon dioxide; and a recovery tank configured to store therein the reused carbon dioxide produced by the purifier, wherein the purifier includes a first purifier and a second purifier arranged sequentially and consecutively, wherein the first purifier is configured to remove moisture from the exhaust gas, and wherein the second purifier is configured to remove organic impurities from the exhaust gas.

According to one or more embodiments, the system further includes an analyzer configured to determine whether a purity of the reused carbon dioxide stored in the recovery tank satisfies another predefined reference.

According to one or more embodiments, the blocking device and the analyzer are configured to employ a same purity reference value as the predefined reference.

According to one or more embodiments, the system further includes: a purifier configured to receive the reused carbon dioxide from the second supply tank and remove residual impurities therefrom; and a filter configured to receive the reused carbon dioxide from the purifier, filter the reused carbon dioxide by removing particles inside the reused carbon dioxide, and then provide the filtered reused carbon dioxide to the process apparatus.

According to one or more embodiments, the system further includes: a pipe for connecting the purifier to the filter; and an analyzer connected to the pipe, wherein the analyzer is configured to determine whether a purity of the reused carbon dioxide flowing in the pipe meets the predefined reference.

According to one or more embodiments, the system further includes a boiler that is configured to operate using liquefied natural gas (LNG) as a fuel to discharge additional exhaust gas containing carbon dioxide therefrom, wherein the purifying device is further configured to purify the additional exhaust gas discharged from the boiler, and thus produce additional reused carbon dioxide therefrom and store the produced additional reused carbon dioxide.

According to embodiments, a method for reusing carbon dioxide is provided. The method includes: producing reused carbon dioxide by purifying exhaust gas discharged from a process apparatus; storing the produced reused carbon dioxide in a recovery tank; supplying the reused carbon dioxide from the recovery tank to a first supply tank; supplying the reused carbon dioxide from the first supply tank to a second supply tank; supplying the reused carbon dioxide from the second supply tank to the process apparatus; determining whether a purity of the reused carbon dioxide flowing from the recovery tank to the first supply tank meets a predefined reference; and blocking flow of the reused carbon dioxide from the recovery tank to the first supply tank, based on determining that the purity of the reused carbon dioxide flowing from the recovery tank to the first supply tank does not meet the predefined reference.

According to one or more embodiments, the method further includes supplying the reused carbon dioxide previously stored in the first supply tank to the second supply tank while the flow of the reused carbon dioxide from the recovery tank to the first supply tank is blocked.

According to one or more embodiments, whether the flow of the reused carbon dioxide from the recovery tank to the first supply tank is blocked is based on a control signal, and the method further includes: sampling the reused carbon dioxide in a first pipe that connects the recovery tank to the first supply tank; analyzing the sampled reused carbon dioxide to generate an analyzing result; and generating the control signal based on the analyzing result.

According to one or more embodiments, the purifying the exhaust gas discharged from the process apparatus includes: collecting the exhaust gas; removing moisture from the collected exhaust gas; removing organic impurities from the collected exhaust gas to produce the reused carbon dioxide; and storing the produced reused carbon dioxide in the recovery tank.

According to one or more embodiments, the method further includes determining whether the reused carbon dioxide stored in the recovery tank satisfies the predefined reference.

According to one or more embodiments, the predefined reference related to the purity of the reused carbon dioxide flowing from the recovery tank to the first supply tank and the predefined reference related to the purity of the reused carbon dioxide stored in the recovery tank are equal to each other.

According to one or more embodiments, the method further includes: receiving the reused carbon dioxide from the second supply tank; removing residual impurities from the reused carbon dioxide that is received from the second supply tank; and supplying the reused carbon dioxide, from which the residual impurities is removed, to the process apparatus.

According to one or more embodiments, the method further includes determining whether a purity of the reused carbon dioxide, from which the residual impurities have been removed, satisfies the predefined reference.

According to one or more embodiments, the method further includes: combusting liquefied natural gas (LNG) as a fuel to discharge additional exhaust gas containing carbon dioxide; and purifying the discharged additional exhaust gas, and producing additional reused carbon dioxide therefrom, and storing the additional reused carbon dioxide.

According to embodiments, a system for reusing carbon dioxide is provided. The system includes: a process apparatus configured to discharge exhaust gas containing carbon dioxide therefrom; a purifying device configured to purify the exhaust gas, and thus produce reused carbon dioxide from the exhaust gas and store the produced reused carbon dioxide; a first analyzer configured to analyze the reused carbon dioxide stored in the purifying device to determine whether a purity thereof meets a predefined reference; a first supply tank configured to receive the reused carbon dioxide from the purifying device; a first pipe that connects the purifying device to the first supply tank; a sampler configured to sample the reused carbon dioxide in the first pipe; a second analyzer configured to analyze the sampled reused carbon dioxide to determine whether a purity thereof meets the predefined reference, and generate an analysis result based on an analyzing result of the purity of the sampled reused carbon dioxide; a controller configured to receive the analyzing result and provide a control signal based on the analyzing result to a valve; the valve, the valve installed at the first pipe and configured to block flow of the reused carbon dioxide to the first supply tank based on the control signal; and a second supply tank configured to receive the reused carbon dioxide from the first supply tank and supply the reused carbon dioxide to the process apparatus.

According to one or more embodiments, the system further includes a boiler that is configured to operate using liquefied natural gas (LNG) as a fuel to discharge additional exhaust gas containing carbon dioxide therefrom, wherein the purifying device is further configured to purify the additional exhaust gas discharged from the boiler, and thus produce additional reused carbon dioxide therefrom and store the produced additional reused carbon dioxide.

Other features and embodiments may be apparent from the following detailed description, the drawings, and the claims.

BRIEF DESCRIPTION OF DRAWINGS

The above and other aspects and features of the present disclosure will become more apparent by describing in detail non-limiting example embodiments thereof with reference to the attached drawings, in which.

DETAILED DESCRIPTIONS

For simplicity and clarity of illustration, elements in the drawings are not necessarily drawn to scale. The same reference numbers in different drawings represent the same or similar elements, and as such perform similar functionality. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure. Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure.

The terminology used herein is for the purpose of describing particular embodiments only and is not intended to limit the present disclosure. As used herein, the singular forms "a" and "an" are intended to include the plural forms as well, unless the context clearly indicates otherwise. It will be further understood that the terms "comprise", "comprising", "include", and "including" when used in this specification, specify the presence of the stated features, integers, operations, elements, and/or components, but do not preclude the presence or addition of one or more other features, integers, operations, elements, components, and/or portions thereof.

As used herein, the term "and/or" includes any and all combinations of one or more of the associated listed items. Expression such as "at least one of" when preceding a list of elements may modify the entirety of list of elements and may not modify the individual elements of the list. When referring to "C to D", this means C inclusive to D inclusive unless otherwise specified.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

It will be understood that when an element or layer is referred to as being "connected to", or "coupled to" another element or layer, it may be directly on, connected to, or coupled to the other element or layer, or one or more intervening elements or layers may be present. In addition, it will also be understood that when an element or layer is referred to as being "between" two elements or layers, it may be the only element or layer between the two elements or layers, or one or more intervening elements or layers may also be present.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In one example, when a certain embodiment may be implemented differently, a function or operation specified in a specific block may occur in a sequence different from that specified in a flowchart. For example, two consecutive blocks may be actually executed at the same time. Depending on a related function or operation, the blocks may be executed in a reverse sequence.

In descriptions of temporal relationships, for example, temporal precedent relationships between two events such as "after", "subsequent to", "before", etc., another event may occur therebetween unless "directly after", "directly subsequent" or "directly before" is indicated. The features of the various embodiments of the present disclosure may be partially or entirely combined with each other, and may be technically associated with each other or operate with each other. The embodiments may be implemented independently of each other and may be implemented together in an association relationship.

Hereinafter, non-limiting example embodiments according to the technical spirit of the present disclosure will be described with reference to the accompanying drawings.

Figure 1:
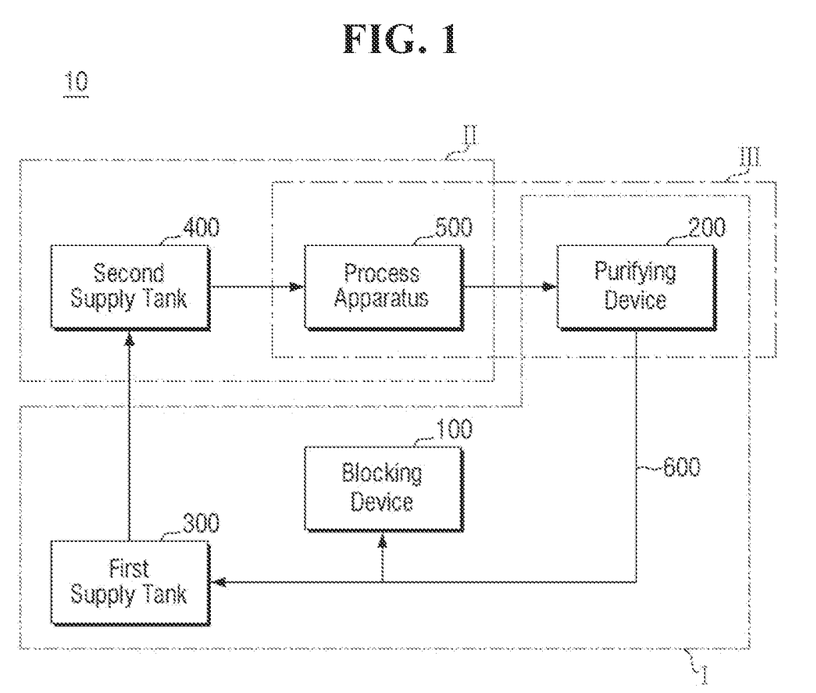
FIG. 1 is a conceptual block diagram of a carbon dioxide reusing system according to some embodiments.

FIG. 1 is a conceptual block diagram of a carbon dioxide reusing system according to some embodiments;

Referring to FIG. 1, a carbon dioxide reusing system 10 may include a blocking device 100, a purifying device 200, a first supply tank 300, a second supply tank 400, a process apparatus 500, and a first pipe 600.

When a purity of the reused carbon dioxide flowing from the purifying device 200 to the first supply tank 300 does not satisfy a predefined reference, the blocking device 100 may block flow of the reused carbon dioxide to the first supply tank 300.

The purifying device 200 may purify an exhaust gas from the process apparatus 500 to produce the reused carbon dioxide and store therein the same before the supply to the first supply tank 300.

The first supply tank 300 may receive the purified reused carbon dioxide from the purifying device 200. The first supply tank 300 may store therein the reused carbon dioxide received from the purifying device 200 and may supply the reused carbon dioxide to the second supply tank 400 as needed.

The second supply tank 400 may receive the reused carbon dioxide from the first supply tank 300. Further, when the flow of the reused carbon dioxide provided from the purifying device 200 to the first supply tank 300 is prevented, the second supply tank 400 may receive carbon dioxide that has a purity that satisfies the predefined reference from an outside.

The second supply tank 400 may store therein carbon dioxide in a supercritical or liquid state. The second supply tank 400 may include a supply pump and a buffer tank to smoothly supply the stored carbon dioxide, and a vaporizer to vaporize the stored carbon dioxide as needed.

The second supply tank 400 may provide, to the process apparatus 500, the reused carbon dioxide provided from the first supply tank 300 or carbon dioxide whose the purity satisfies the predefined reference provided from the outside.

The process apparatus 500 may receive the reused carbon dioxide from the second supply tank 400 or carbon dioxide provided from the outside.

The process apparatus 500 may perform semiconductor processes. Specifically, for example, the carbon dioxide used in the process apparatus 500 may be input to the process apparatus 500 to discharge isopropyl alcohol (IPA) used in a semiconductor substrate cleaning process out of the process apparatus 500. Alternatively, for example, the carbon dioxide used in the process apparatus 500 may be used to control a refractive index of irradiated light and to treat bubbles generated in that process in semiconductor exposure process (photolithography). However, embodiments of the present disclosure are not limited thereto.

In the carbon dioxide reusing system 10, the carbon dioxide may flow through a pipe. For example, the reused carbon dioxide flowing from purifying device 200 to the first supply tank 300 may travel through the first pipe 600.

Figure 2:
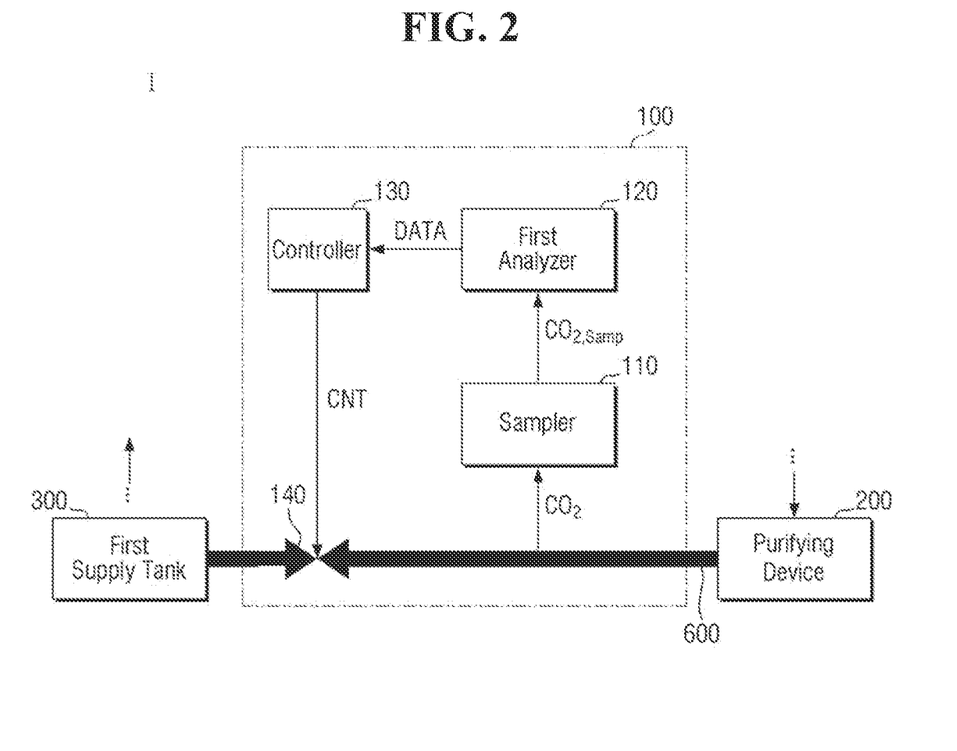
FIG. 2 is an enlarged view of an area I for illustrating a configuration and an operation of the blocking device of FIG. 1 according to some embodiments.

FIG. 2 is an enlarged view of an area I for illustrating a configuration and an operation of the blocking device of FIG. 1 according to some embodiments.

Referring to FIG. 2, the blocking device 100 may include a sampler 110, a first analyzer 120, a controller 130, and a valve 140.

The sampler 110 may sample a portion of the reused carbon dioxide $CO_2$ moving from the purifying device 200 to the first supply tank 300 through the first pipe 600. The sampler 110 may provide the sampled reused carbon dioxide $CO_{2,Samp}$ to the first analyzer 120.

The first analyzer 120 may receive the reused carbon dioxide $CO_{2,Samp}$ sampled from the sampler 110 and analyze a purity of the sampled reused carbon dioxide $CO_{2,Samp}$. The first analyzer 120 may determine whether the purity of the sampled reused carbon dioxide $CO_{2,Samp}$ satisfies the predefined reference. The first analyzer 120 may produce the analyzing result data of the sampled reused carbon dioxide $CO_{2,Samp}$ and provide the result data to the controller 130.

The predefined reference of the purity of the reused carbon dioxide may mean the purity of carbon dioxide suitable for the semiconductor processes. Specifically, the reference of the purity of the reused carbon dioxide may set to 99.9999%.

More specifically, in order to ensure that the purity of the reused carbon dioxide is suitable for the semiconductor process, the first analyzer 120 may set a reference so that a concentration of each of various impurities present inside the reused carbon dioxide is below a certain value, and may determine whether a concentration of each of the impurities as obtained using an analyzing method of each of the impurities meets the predefined reference. For example, a reference of a concentration of nitrogen gas inside the reused carbon dioxide may be set to 0.235 ppm, and then whether an actual concentration of nitrogen gas as measured meets the reference may be determined. Further, the first analyzer 120 may use a gas chromatography (GC) to analyze the nitrogen gas concentration inside the reused carbon dioxide. However, embodiments of the present disclosure are not limited thereto.

The controller 130 may receive the analyzing result data from the first analyzer 120. The controller 130 may provide the valve 140 with a control signal CNT that controls opening and closing of the valve 140 based on the analyzing result data.

The control signal CNT may include a supply-maintaining signal to maintain the supply of the reused carbon dioxide from the purifying device 200 to the first supply tank 300, and a supply-stopping signal to stop the supply of the reused carbon dioxide from the purifying device 200 to the first supply tank 300. However, embodiments of the present disclosure are not limited thereto.

The valve 140 may receive the control signal CNT from the controller 130, and may open or close the first pipe 600 based on the control signal CNT. In this connection, the first pipe 600 may act as a passage along which the reused carbon dioxide flows from the purifying device 200 to the first supply tank 300.

When the out-of-reference purity (e.g. less than a predetermined purity) of the reused carbon dioxide provided from the purifying device 200 is detected based on the analyzing result of the purity of the reused carbon dioxide in real time by the first analyzer 120, the reused carbon dioxide having the out-of-reference purity may not be provided to the first supply tank 300. Accordingly, the first supply tank 300 may provide the reused carbon dioxide of a purity that satisfies the predefined reference and has been stored previously therein to the second supply tank. Therefore, the problem that may occur due to the out-of-reference-purity in the process apparatus may be avoided.

Further, even when the supply of the reused carbon dioxide from the purifying device 200 to the first supply tank 300 is stopped due to the out-of-reference purity, the first supply tank 300 may continue to supply the reused carbon dioxide to the process apparatus through the second supply tank. Therefore, a problem that may occur in the process apparatus due to the stop of the carbon dioxide supply may be prevented.

Figure 3:
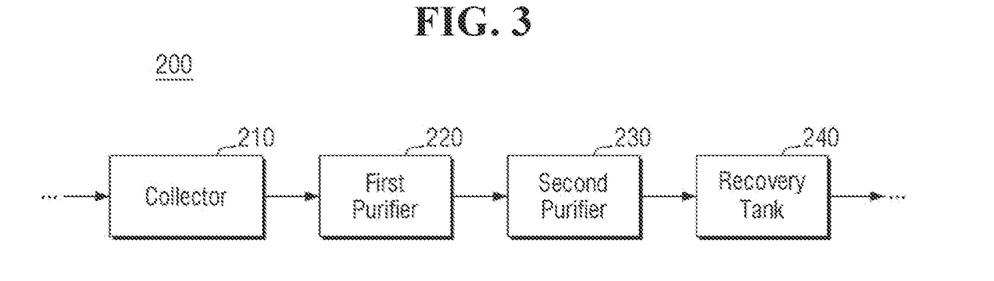
FIG. 3 is a conceptual block diagram of the purifying device of FIG. 1 according to some embodiments.

FIG. 3 is a conceptual block diagram of the purifying device of FIG. 1 according to some embodiments.

Referring to FIG. 3, the purifying device 200 may include a collector 210, a first purifier 220, a second purifier 230, and a recovery tank 240.

The collector 210 may collect exhaust gas discharged from the process apparatus 500 and provide the collected gas to the first purifier 220.

The first purifier 220 may purify the carbon dioxide inside the exhaust gas provided from the collector 210 to remove moisture inside the exhaust gas for reusing. The first purifier 220 may provide the exhaust gas from which the moisture has been removed to the second purifier 230.

The first purifier 220 may remove the moisture inside the exhaust gas using a phase separating scheme. Specifically, the first purifier 220 may include a compressor that compresses the received carbon dioxide to increase a dew point thereof, a cooler that cools the compressed carbon dioxide to condense moisture, and an expander which expands the carbon dioxide again to separate the carbon dioxide and the moisture from each other and removes the condensed moisture. However, embodiments of the present disclosure are not limited thereto.

The second purifier 230 may be configured to perform further purification after the first purifier 220. Thus, the second purifier 230 may receive the moisture-removed exhaust gas from the first purifier 220 and remove organic impurities from the exhaust gas. The second purifier 230 may remove impurities inside the exhaust gas to produce the reused carbon dioxide and may supply the produced reused carbon dioxide to the recovery tank 240.

The second purifier 230 may remove the impurities such as organic contaminants and metal residues having different boiling points from that of the carbon dioxide via distillation, adsorption, or catalytic oxidation.

Specifically, the second purifier 230 may condense carbon dioxide to produce condensed liquid and then concentrate contaminants into the condensed liquid, thereby to removing the impurities therefrom. Alternatively, the second purifier 230 may use activated carbon to allow organic matter to be absorbed into the activated carbon to remove the impurities. Alternatively, the second purifier 230 may inject an oxidizing agent such as oxygen as catalyst into the exhaust gas to remove the impurities therefrom. However, embodiments of the present disclosure are not limited thereto.

In one example, the second purifier 230 may include an outlet for discharging the purified exhaust gas at a distal end thereof. That is, when the out-of-reference purity of the purified reused carbon dioxide is detected due to a problem inside the carbon dioxide reusing system, the distal end of the second purifier 230 may be configured to discharge the purified exhaust gas to an outside.

Accordingly, when the first purifier 220 and the second purifier 230 fail to purify the reused carbon dioxide so that the purity of the purified carbon dioxide satisfies the predefined reference, the flow of the reused carbon dioxide from the recovery tank 240 to the first supply tank may be blocked. Correspondingly, the distal end of the second purifier 230 may discharge the reused carbon dioxide having the out-of-reference purity to the outside so that the supply of the reused carbon dioxide having the out-of-reference purity from the second purifier 230 to the recovery tank 240 may be stopped.

The recovery tank 240 may store therein the reused carbon dioxide produced by the second purifier 230. The stored reused carbon dioxide may be supplied to the first supply tank 300 through the first pipe 600. The recovery tank 240 may include a liquefied state maintaining device and a vaporizer to maintain or change a phase of carbon dioxide as required.

Figure 4:
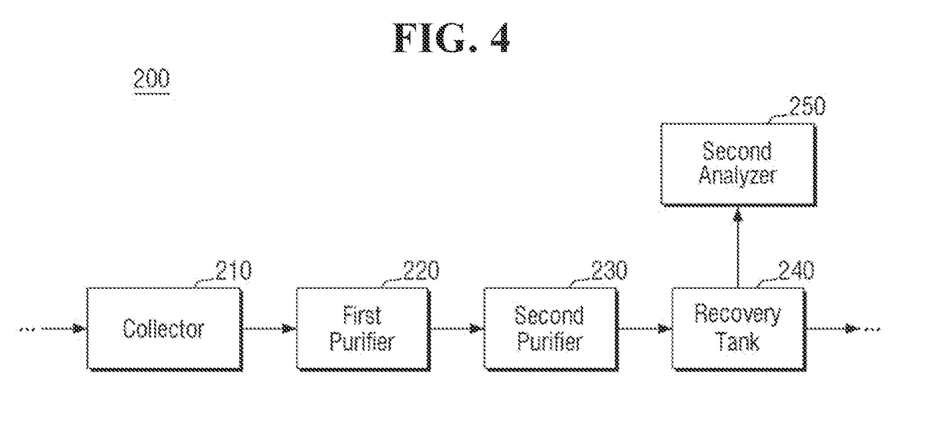
FIG. 4 is a conceptual block diagram of the purifying device of FIG. 1 according to further some embodiments.

FIG. 4 is a conceptual block diagram of the purifying device 200 of FIG. 1 according to some embodiments.

Referring to FIG. 4, a second analyzer 250 may be connected to the recovery tank 240.

The second analyzer 250 may determine whether the purity of the reused carbon dioxide produced from the second purifier 230 and then stored in the recovery tank 240 satisfies the predefined reference.

The predefined reference and the impurities analyzing method from the reused carbon dioxide related to the second analyzer 250 may be the same as those related to the first analyzer 120. That is, the first analyzer 120 and the second analyzer 250 may employ the same reference and the same analyzing method.

Therefore, before the purified reused carbon dioxide is fed to the process apparatus 500 through the first supply tank 300 and the second supply tank 400, the purified reused carbon dioxide may be subjected to at least two analyses using at least two analyzers. This may prevent the reused carbon dioxide having the out-of-reference purity from being provided to the process apparatus 500. That is, when one of the first analyzer 120 and the second analyzer 250 malfunctions to cause an error in the purity analyzing result, the other of the first analyzer 120 and the second analyzer 250 may correctly function to analyze the purity thereof, thereby preventing the reused carbon dioxide having the out-of-reference purity from being provided to the process apparatus 500.

Figure 5:
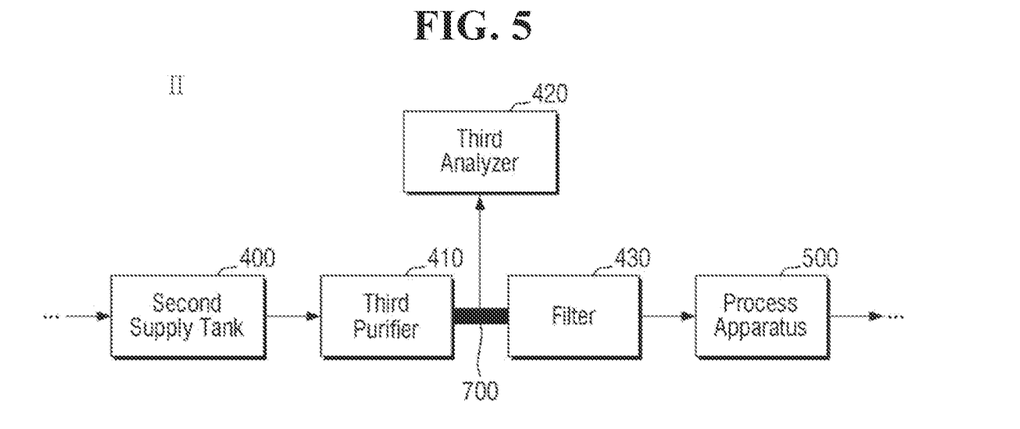
FIG. 5 is an enlarged view of an area II to illustrate components between the second supply tank and the process apparatus of FIG. 1 according to some embodiments.

FIG. 5 is an enlarged view of an area II to illustrate components between the second supply tank 400 and the process apparatus 500 of FIG. 1 according to some embodiments.

A third purifier 410, a third analyzer 420, a filter 430, and a second pipe 700 may be disposed between the second supply tank 400 and the process apparatus 500.

The third purifier 410 may receive the reused carbon dioxide from the second supply tank 400 and then remove residual impurities therefrom. That is, the third purifier 410 may be configured to perform additional purifying to ensure that the purity of the reused carbon dioxide is suitable for the process apparatus 500 before the reused carbon dioxide is supplied to the process apparatus 500.

The reused carbon dioxide purified from the third purifier 410 may flow to the filter 430 through the second pipe 700. The third analyzer 420 may analyze the reused carbon dioxide flowing through the second pipe 700.

The third analyzer 420 may employ the same reference and the same analyzing method as those of each of the first analyzer 120 and the second analyzer 250.

The filter 430 may receive the purified reused carbon dioxide from the third purifier 410 through the second pipe 700, and may remove particles that may exist in the reused carbon dioxide via filtering. The filter 430 may finally provide the reused carbon dioxide to the process apparatus 500.

Additionally placing the third purifier 410, the third analyzer 420, and the filter 430 upstream of the process apparatus 500 may allow the reused carbon dioxide of reliable purity to be provided to the process apparatus 500.

Figure 6:
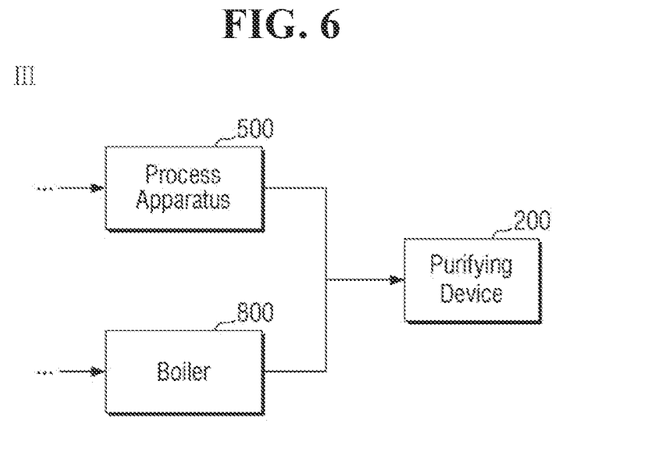
FIG. 6 is an enlarged view to specifically illustrate an area III of FIG. 1.

FIG. 6 is an enlarged view to specifically illustrate an area III of FIG. 1.

Referring to FIG. 6, the purifying device 200 may purify the exhaust gas discharged from the boiler 800 together with the exhaust gas discharged from the process apparatus 500 to produce the reused carbon dioxide.

The boiler 800 may include a component that operates using liquefied natural gas (LNG) as a fuel in addition to the process apparatus 500.

When the purifying device 200 may collect and purify not only the exhaust gas discharged from the process apparatus 500 but also the exhaust gas discharged from the boiler 800, an amount of carbon dioxide emitted into an atmosphere may be reduced. Further, an amount of the reused carbon dioxide may increase, thereby preventing supply and demand risk due to external influences on a carbon dioxide supply chain.

Figure 7:
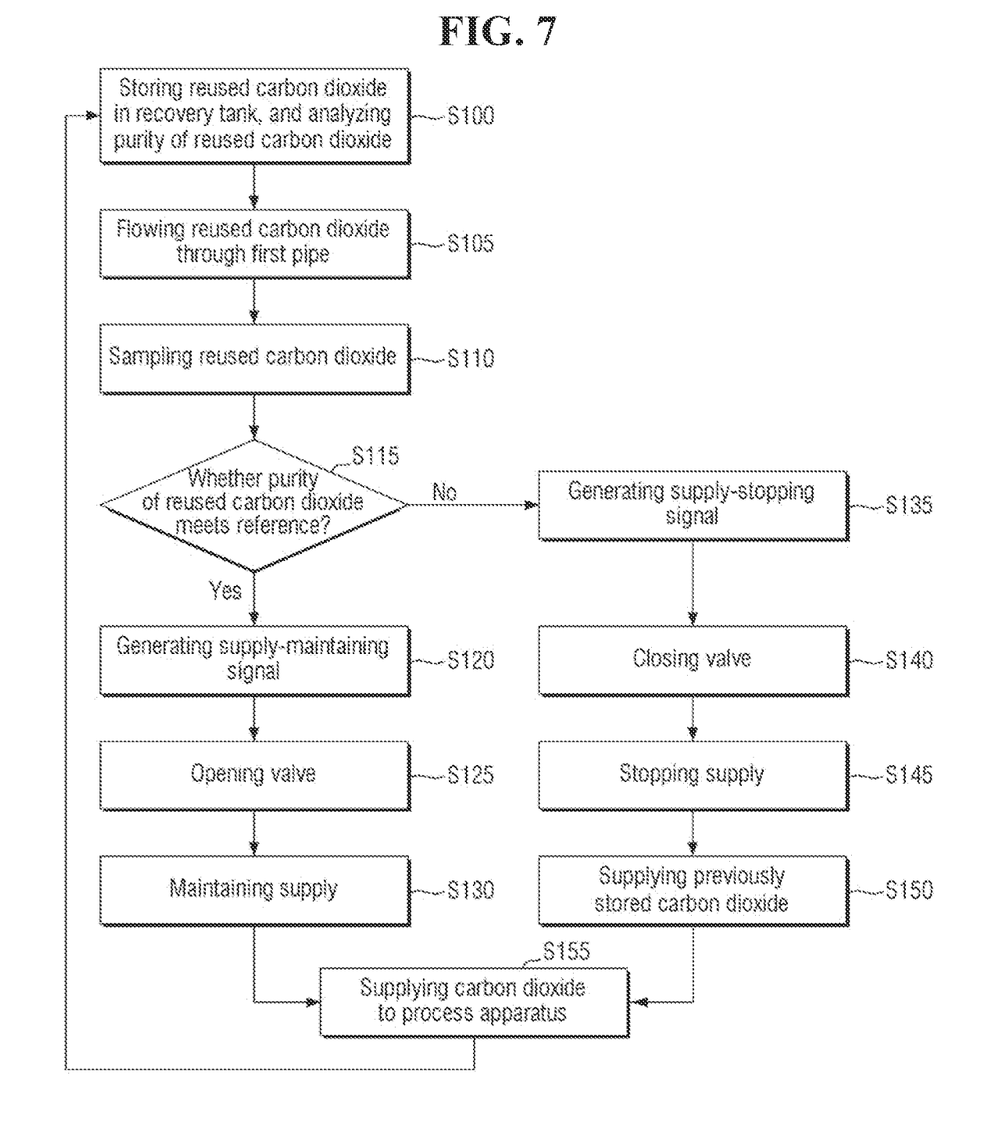
FIG. 7 is an example flowchart for illustrating an operation of the carbon dioxide reusing system of FIG. 1 according to some embodiments.

FIG. 7 is an example flowchart for illustrating an operation of the carbon dioxide reusing system of FIG. 1 according to some embodiments.

Referring to FIG. 7, first, carbon dioxide may be used in the process apparatus 500 and then, may be discharged in a form of exhaust gas. The purifying device 200 may purify the exhaust gas to produce the reused carbon dioxide which in turn may be stored in the recovery tank 240, and then, the reused carbon dioxide stored in the recovery tank 240 may be analyzed by the second analyzer 250 in S100.

Subsequently, the reused carbon dioxide introduced into the recovery tank 240 may flow to the first supply tank 300 through the first pipe 600 in S105.

While the reused carbon dioxide flows to the first supply tank 300 through the first pipe 600, the sampler 110 may sample the reused carbon dioxide flowing through the first pipe 600 in S110.

The sampled reused carbon dioxide may be provided to the first analyzer 120, the first analyzer 120 may determine whether a purity of the reused carbon dioxide meets the predefined reference in real time, and then, the analyzing result may be provided to a controller 130 in S115.

When the purity of the reused carbon dioxide satisfies the predefined reference, based on the result of analyzing, the controller 130 may generate the supply-maintaining signal and provide the signal to the valve 140 in S120.

The valve 140 may receive the supply-maintaining signal, and thus, the valve 140 may be opened in response to the supply-maintaining signal in S125.

Accordingly, the supply of the reused carbon dioxide from the purifying device 200 to the first supply tank 300 may be maintained. Sequentially, the reused carbon dioxide may be provided from the first supply tank 300 to the second supply tank 400 in S130.

Subsequently, the reused carbon dioxide provided to the second supply tank 400 may be supplied to the process apparatus 500, and then may be used therein, and then may be discharged again in a form of the exhaust gas and thus may be introduced into the purifying device 200 in S155.

To the contrary, when the purity of the reused carbon dioxide does not satisfy the predefined reference, based on the result of analyzing, the controller 130 may generate the supply-stopping signal and provide the signal to the valve 140 in S135.

The valve 140 may receive the supply-stopping signal, and thus the valve 140 may be closed in response to the supply-stopping signal in S140.

Accordingly, the supply of the reused carbon dioxide from the purifying device 200 to the first supply tank 300 may be blocked in S145. Further, when the reused carbon dioxide supply to the first supply tank 300 is blocked, the distal end of the second purifier 230 may discharge the purified exhaust gas to the outside.

Subsequently, the first supply tank 300 may provide, to the second supply tank 400, the reused carbon dioxide whose the purity meets the predefined reference and which has previously received from the purifying device 200 and stored therein in S150. Further, the second supply tank 400 may receive carbon dioxide whose the purity meets the predefined reference from the outside.

Subsequently, the carbon dioxide supplied to the second supply tank 400 may be supplied to the process apparatus 500, and may be used therein, and then may be discharged again in a form of exhaust gas and then may be introduced into the purifying device 200 in S155.

When the purity of the carbon dioxide is out of the reference due to the malfunction of the carbon dioxide reusing system 10, the carbon dioxide of the out-of-reference purity may be discharged from the distal end of the purifying part to the outside. Therefore, this may prevent the poor-quality carbon dioxide from continuously flowing into the storage, flowing from the storage to the supplier, and then being supplied to the process apparatus 500.

In addition, the controller 130 may control a flow rate control valve (e.g. valve 140) to block the inflow of the carbon dioxide from the recovery tank 240 to the first supply tank 300. Thus, even when there is no additional supply of the purified carbon dioxide to the first supply tank 300, the first supply tank 300 may supply, to the process apparatus 500, the carbon dioxide whose the purity meets the reference and which has previously received from the first supply tank 300 or the outside and stored therein. This may prevent a risk in the process apparatus 500 due to the interruption of the process.

In concluding the detailed description, those skilled in the art will appreciate that many variations and modifications may be made to the non-limiting example embodiments without departing from the principles of the present disclosure. Therefore, the described non-limiting example embodiments are used in a general and descriptive sense only and not for purposes of limitation.

What is claimed is:

1. A system for reusing carbon dioxide, the system comprising:
   a process apparatus configured to discharge exhaust gas containing carbon dioxide therefrom;
   a purifying device configured to purify the exhaust gas, and thus produce reused carbon dioxide from the exhaust gas and store the produced reused carbon dioxide;
   a first supply tank configured to receive the reused carbon dioxide from the purifying device;
   a second supply tank configured to receive the reused carbon dioxide from the first supply tank and provide the reused carbon dioxide to the process apparatus; and
   a blocking device configured to:
      determine whether a purity of the reused carbon dioxide provided from the purifying device to the first supply tank satisfies a predefined reference; and
      based on determining that the purity of the reused carbon dioxide provided from the purifying device to the first supply tank fails to satisfy the predefined reference, block flow of the reused carbon dioxide from the purifying device to the first supply tank.

2. The system of claim 1, wherein while the blocking device blocks the flow of the reused carbon dioxide, the first supply tank is configured to provide previously stored reused carbon dioxide therein to the second supply tank.

3. The system of claim 1, wherein the system further comprises:
   a first pipe that connects the purifying device to the first supply tank; and
   a valve installed at the first pipe, the valve configured to block the flow of the reused carbon dioxide to the first supply tank,
   wherein the blocking device comprises:
      a sampler configured to sample the reused carbon dioxide in the first pipe;

a first analyzer configured to determine whether the purity of the sampled reused carbon dioxide satisfies the predefined reference, and generate an analyzing result of the purity of the sampled reused carbon dioxide; and a controller configured to receive the analyzing result and provide a control signal based on the analyzing result to the valve.

4. The system of claim 1, wherein the purifying device comprises:

a collector configured to collect the exhaust gas;

a purifier configured to purify the collected exhaust gas to produce the reused carbon dioxide; and a recovery tank configured to store therein the reused carbon dioxide produced by the purifier, wherein the purifier comprises a first purifier and a second purifier arranged sequentially and consecutively, wherein the first purifier is configured to remove moisture from the exhaust gas, and wherein the second purifier is configured to remove organic impurities from the exhaust gas.

5. The system of claim 4, wherein the system further comprises an analyzer configured to determine whether a purity of the reused carbon dioxide stored in the recovery tank satisfies another predefined reference.

6. The system of claim 5, wherein the blocking device and the analyzer are configured to employ a same purity reference value as the predefined reference.

7. The system of claim 1, wherein the system further comprises:

a purifier configured to receive the reused carbon dioxide from the second supply tank and remove residual impurities therefrom; and a filter configured to receive the reused carbon dioxide from the purifier, filter the reused carbon dioxide by removing particles inside the reused carbon dioxide, and then provide the filtered reused carbon dioxide to the process apparatus.

8. The system of claim 7, wherein the system further comprises:

a pipe for connecting the purifier to the filter; and an analyzer connected to the pipe, wherein the analyzer is configured to determine whether a purity of the reused carbon dioxide flowing in the pipe meets the predefined reference.

9. The system of claim 1, wherein the system further comprises a boiler that is configured to operate using liquefied natural gas (LNG) as a fuel to discharge additional exhaust gas containing carbon dioxide therefrom, wherein the purifying device is further configured to purify the additional exhaust gas discharged from the boiler, and thus produce additional reused carbon dioxide therefrom and store the produced additional reused carbon dioxide.

10. A system for reusing carbon dioxide, the system comprising:

a process apparatus configured to discharge exhaust gas containing carbon dioxide therefrom;

a purifying device configured to purify the exhaust gas, and thus produce reused carbon dioxide from the exhaust gas and store the produced reused carbon dioxide;

a first analyzer configured to analyze the reused carbon dioxide stored in the purifying device to determine whether a purity thereof meets a predefined reference;

a first supply tank configured to receive the reused carbon dioxide from the purifying device;

a first pipe that connects the purifying device to the first supply tank;

a sampler configured to sample the reused carbon dioxide in the first pipe;

a second analyzer configured to analyze the sampled reused carbon dioxide to determine whether a purity thereof meets the predefined reference, and generate an analysis result based on an analyzing result of the purity of the sampled reused carbon dioxide;

a controller configured to receive the analyzing result and provide a control signal based on the analyzing result to a valve;

the valve, the valve installed at the first pipe and configured to block flow of the reused carbon dioxide to the first supply tank based on the control signal; and a second supply tank configured to receive the reused carbon dioxide from the first supply tank and supply the reused carbon dioxide to the process apparatus.

11. The system of claim 10, wherein the system further comprises a boiler that is configured to operate using liquefied natural gas (LNG) as a fuel to discharge additional exhaust gas containing carbon dioxide therefrom, wherein the purifying device is further configured to purify the additional exhaust gas discharged from the boiler, and thus produce additional reused carbon dioxide therefrom and store the produced additional reused carbon dioxide.

* * * * *